United States Patent [19]
Nicholas et al.

[11] Patent Number: 5,967,974
[45] Date of Patent: Oct. 19, 1999

[54] SURGICAL RETRACTOR

[75] Inventors: David A. Nicholas, Trumbull; Richard D. Gresham, Monroe; Thomas R. Hessler, Bethel; Patrick Flanagan, Stratford; Hanspeter R. Bayer, Meriden, all of Conn.

[73] Assignee: United States Surgical Corporation, Norwalk, Conn.

[21] Appl. No.: 08/994,686

[22] Filed: Dec. 19, 1997

Related U.S. Application Data

[60] Provisional application No. 06/045,487, May 2, 1997.

[51] Int. Cl.[6] ................................................. A61B 17/02
[52] U.S. Cl. ........................................... 600/233; 600/228
[58] Field of Search .................................... 600/231, 232, 600/233, 228

[56] References Cited

U.S. PATENT DOCUMENTS

| | | |
|---|---|---|
| Re. 34,150 | 12/1992 | Santilli et al. . |
| 1,400,616 | 12/1921 | McCrory et al. . |
| 1,963,173 | 6/1934 | Morin ...................................... 600/233 |
| 2,594,086 | 4/1952 | Smith . |
| 2,623,517 | 12/1952 | Barlow ..................................... 600/233 |
| 2,670,732 | 3/1954 | Nelson . |
| 2,751,903 | 6/1956 | Ivory et al. . |
| 2,812,759 | 11/1957 | Taylor . |
| 3,040,739 | 6/1962 | Grieshaber .............................. 600/233 |
| 3,965,890 | 6/1976 | Gauthier . |
| 3,998,217 | 12/1976 | Trumbull et al. ........................ 600/233 |
| 4,254,763 | 3/1981 | McCready et al. ...................... 600/231 |
| 4,380,999 | 4/1983 | Healy . |
| 4,457,300 | 7/1984 | Budde . |
| 4,627,421 | 12/1986 | Symbas et al. . |
| 4,702,230 | 10/1987 | Pelta . |
| 4,726,356 | 2/1988 | Santilli et al. . |
| 4,747,395 | 5/1988 | Brief . |
| 4,813,401 | 3/1989 | Grieshaber . |
| 4,829,985 | 5/1989 | Couetil . |
| 4,852,552 | 8/1989 | Chaux . |
| 4,856,019 | 8/1989 | Phillips . |
| 4,884,559 | 12/1989 | Collins . |
| 4,971,038 | 11/1990 | Farley ..................................... 600/231 |
| 5,000,163 | 3/1991 | Ray et al. . |
| 5,025,779 | 6/1991 | Bugge . |
| 5,231,974 | 8/1993 | Giglio et al. . |
| 5,375,481 | 12/1994 | Cabrera et al. ......................... 600/233 |
| 5,503,617 | 4/1996 | Jako . |
| 5,520,610 | 5/1996 | Giglio et al. . |
| 5,882,299 | 3/1999 | Rastegar et al. . |

FOREIGN PATENT DOCUMENTS

| | | |
|---|---|---|
| 0336526 | 10/1989 | European Pat. Off. . |
| 2102681 | 2/1983 | United Kingdom . |
| 2233561 | 1/1991 | United Kingdom . |

*Primary Examiner*—Paul J. Hirsch

[57] ABSTRACT

A surgical retractor assembly is provided comprising a frame having first and second portions, a first hook member supported on the frame, a second hook member supported on the frame and movable with respect to the frame, and a frame support supporting the frame. The frame support is adapted to retain the first portion of the frame in a selected raised position with respect to the second portion of the frame. The frame support preferably comprises two elongated shafts having locking mechanisms for locking the frame in the selected raised position.

24 Claims, 7 Drawing Sheets

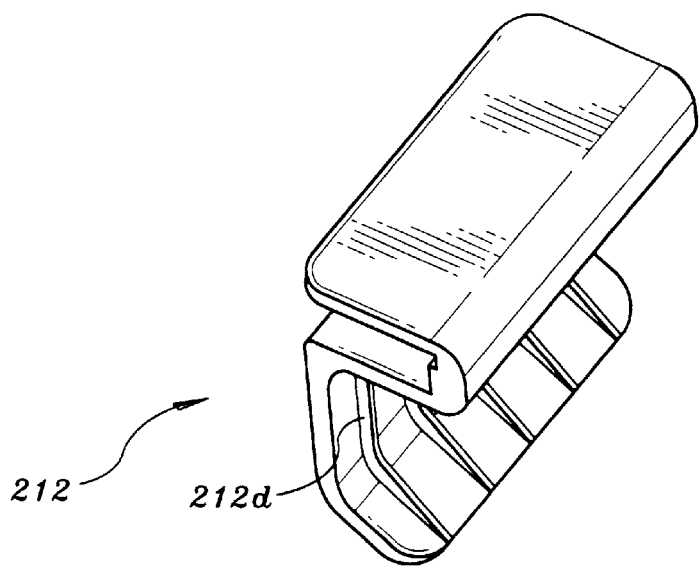
FIG. 16
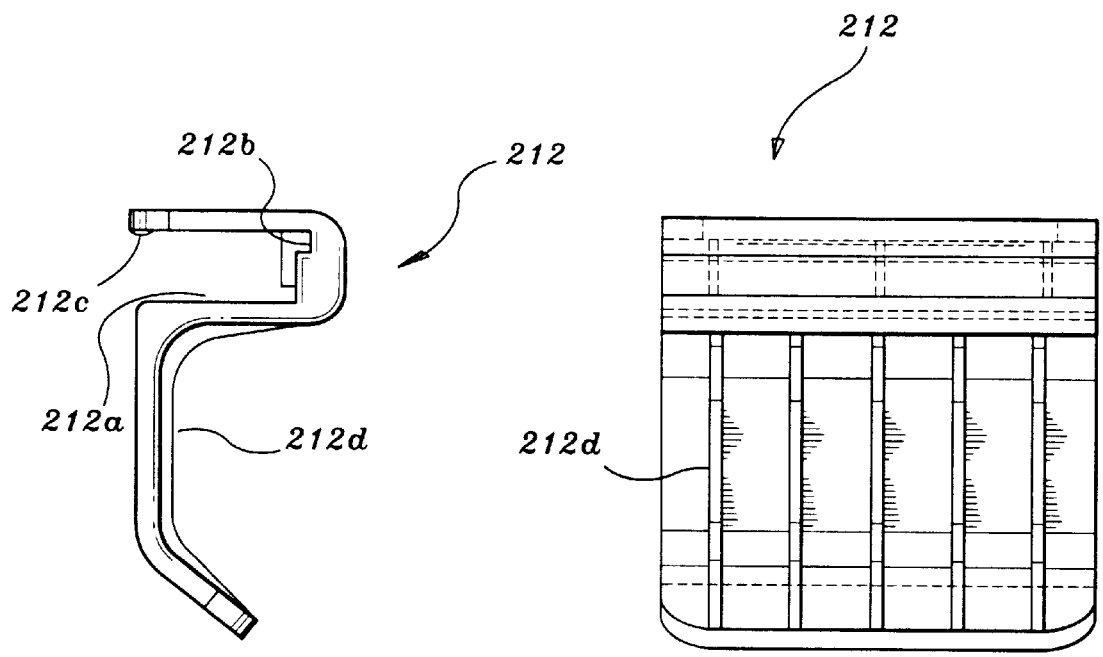
FIG. 17
FIG. 18

SURGICAL RETRACTOR

CROSS REFERENCE TO RELATED APPLICATIONS

This application claims priority to U.S. Provisional Application Serial No. 60/045,487 filed May 2, 1997.

BACKGROUND

1. Technical Field

The disclosure relates to a surgical apparatus and method and more particularly to a minimally invasive surgical apparatus and method for retracting tissue.

2. Background of the Related Art

The diagnosis and treatment of coronary disease and related conditions typically require access to the heart, blood vessels, and associated tissue. Such procedures include cardiopulmonary bypass, valve repair and replacement, and treatment of aneurysms. Until recently, access to the patient's thoracic cavity was achieved by a large longitudinal incision in the chest. This procedure, referred to as a median sternotomy, required a saw or other cutting instrument to cut the sternum and allow two opposing halves of the rib cage to be spread apart U.S. Patent No. to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extended and is often painful. Furthermore, patients for whom coronary surgery is indicated may need to forego such surgery due to the risks involved with gaining access to the heart.

To avoid the risks and pitfalls of median sternotomies, a minimally invasive "window" approach to vascular or cardiac surgery has recently been developed. One example of the window approach is disclosed in European patent application 97106912.5, filed on Apr. 25, 1997. The 97106912.5 application shows an oval shaped retractor having several retractor blades mounted thereon to spread the ribs and allow access to the heart for performing procedures such as coronary bypass.

In certain instances, additional access to other vessels and improved visibility is desirable. One way to achieve this would be to not only spread the retractor blades apart to spread the ribs laterally, but to also spread the ribs and surrounding upwardly away from the body, e.g. to lift the tissue. This would enable additional procedures to be performed through a window approach, such as an "IMA (internal mammary artery) takedown" where the artery is dissected for subsequent attachment to the heart or other vessel to complete the bypass.

SUMMARY

The apparatus and method disclosed herein provides improved surgical access through a minimally invasive window approach. This is achieved by providing a surgical retractor assembly comprising a frame lying in first plane, at least one elevation control supporting the frame and configured to selectively lift at least a portion of the frame out of the first plane, and at least one hook member supported on the frame and configured to retract tissue. A second hook member is preferably removably mounted to the frame and configured to retract tissue in a direction away from the at least one hook member. The elevation control assembly may comprise a pair of elongated shafts removably mounted to the frame with each of the control assemblies including a locking mechanism to retain the frame in the selected position.

A surgical retractor assembly is also provided comprising a frame, a first hook member supported on the frame, a second hook member supported on the frame and movable with respect to the frame, and a frame support supporting the frame and adapted to retain a first portion of the frame in a selected raised position with respect to a second portion of the frame.

A method for accessing the internal mammary artery in a minimally invasive procedure is also provided comprising placing a first hook member supported on a frame between the ribs, placing a second hook member supported on the frame between the ribs, moving the second hook member in a direction away from the first hook member to retract the ribs, elevating a first portion of the frame away from the body to a selected raised position, and retaining the first portion of the frame in the selected raised position. The method may further comprise the step of inserting a dissector through an opening in the frame to dissect the internal mammary artery. The step of elevating the first portion of the frame may comprise the step of manually sliding the first portion of the frame along first and second spaced apart shafts.

BRIEF DESCRIPTION OF THE DRAWINGS

Various embodiments of the presently disclosed surgical retractor apparatus are described herein with reference to the drawing figures wherein:

FIG. 16 is a perspective view of a removable base hook for the surgical retractor apparatus embodiment of FIG. 12;

FIG. 17 is a side-view of the removable base hook of FIG. 16; and

FIG. 18 is a front-view of the removable base hook of FIG. 16.

DETAILED DESCRIPTION OF PREFERRED EMBODIMENTS

The preferred embodiments of the apparatus disclosed herein will be discussed in terms of procedures and apparatus for use in heart surgery. More specifically, the apparatus can be used to enable minimally invasive dissection of the internal mammary artery (IMA) by retracting the ribs to enable access to the IMA. However, the present disclosure should not be limited to an apparatus for use in conjunction with such heart surgery, but may find application in surgery wherein access to the surgical site is achieved through a small incision and retraction of the surrounding tissues and/or bone if desired.

Figure 2:
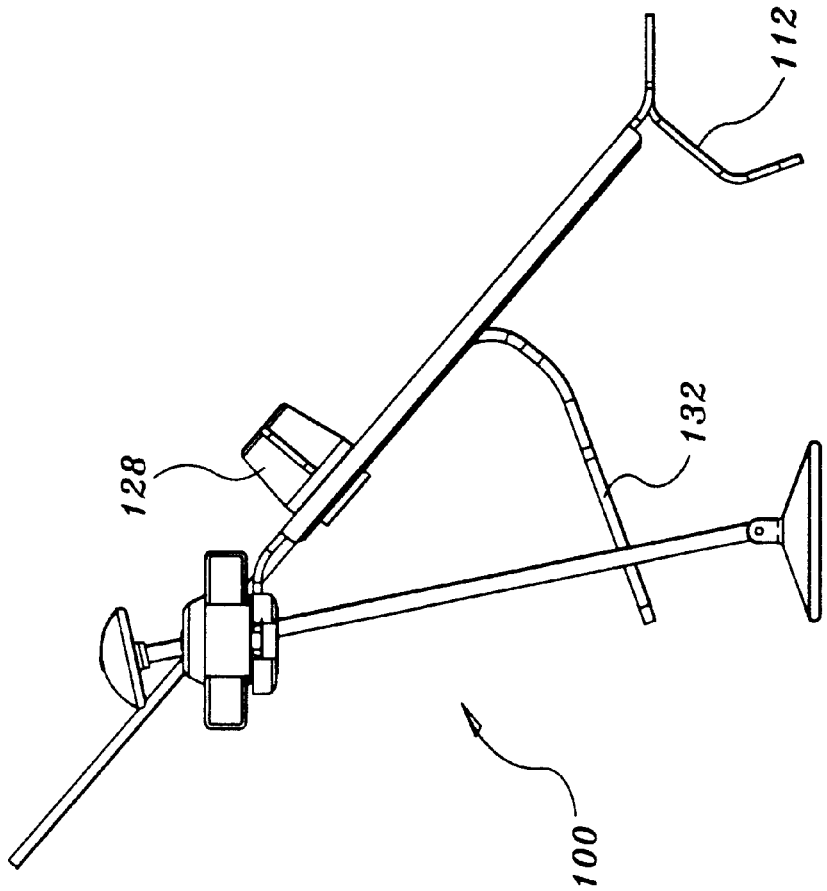
FIG. 2 is a side view of the surgical retractor of FIG. 1.
Figure 1:
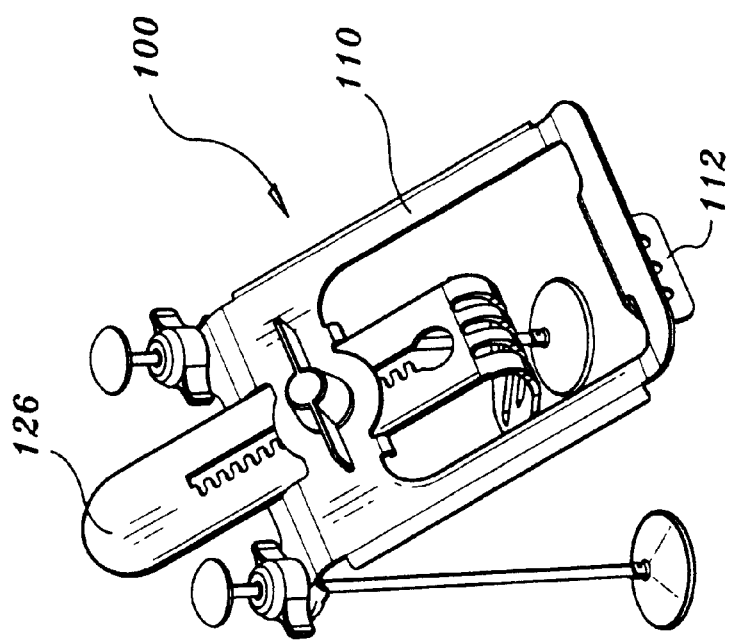
FIG. 1 is a perspective view of a surgical retractor constructed in accordance with a first embodiment of the present disclosure.
Figure 3:
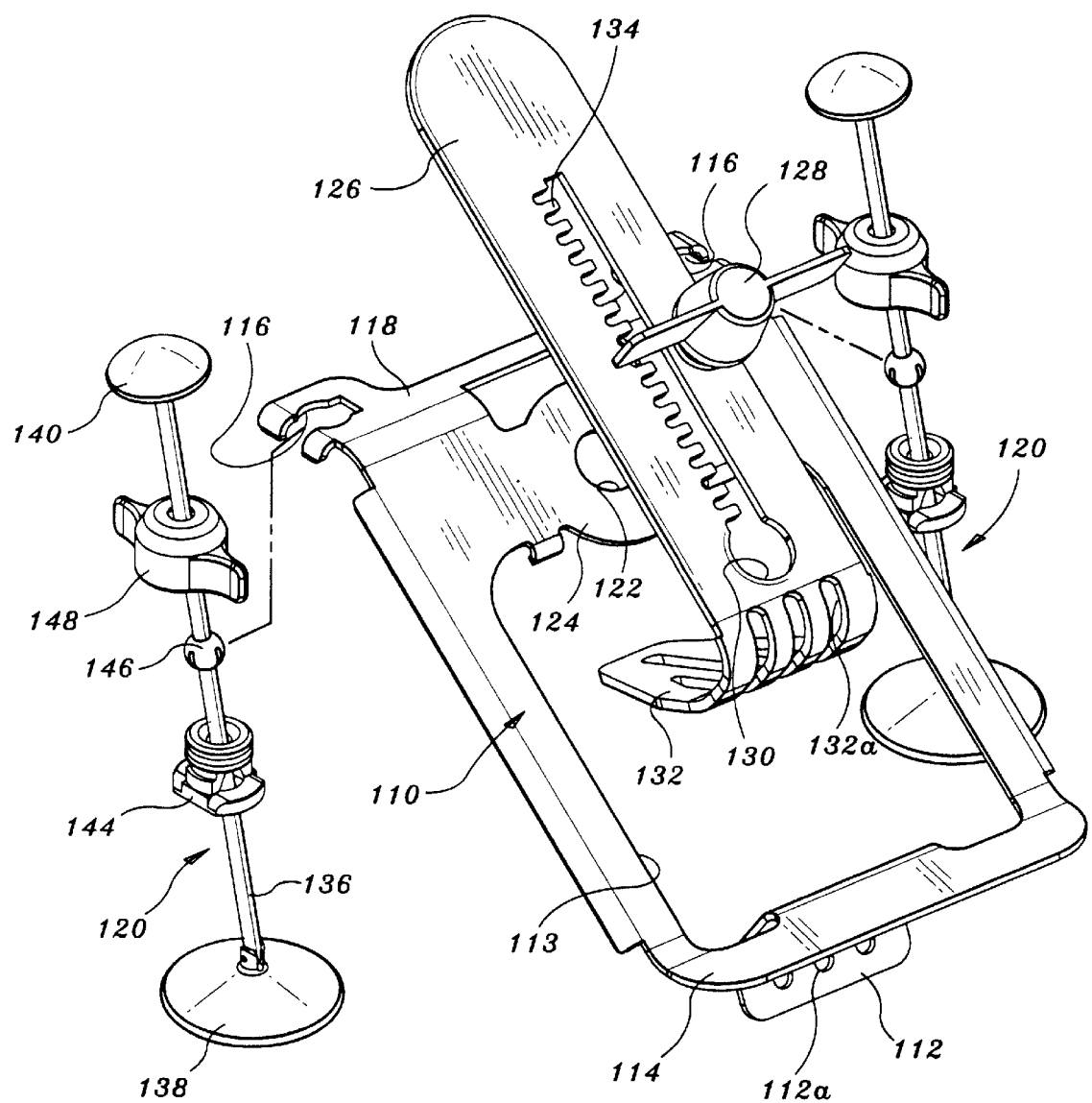
FIG. 3 is an enlarged perspective view with parts separated of the surgical retractor of FIG. 1.

Referring now in detail to the drawings in which like reference numerals identify similar or identical elements, a first embodiment of the surgical retractor of the present disclosure is illustrated in FIGS. 1–3, and is designated generally by reference numeral 100. Surgical retractor 100 has frame member 110 which is preferably formed of a material which is readily sterilizable after use, for example, stainless steel. Alternatively, some or all of the components may be made of disposable materials so that the apparatus could be discarded after use. Frame 110 has various cut-out portions and contours which may be formed by way of stamping frame 110 out of a solid sheet of material.

A fixed hook portion 112 is provided at the lower flattened end portion 114 of frame member 110. Hook portion 112 is preferably provided with slotted openings 112a to facilitate gripping of bone and/or tissue, thereby preventing lateral movement of hook member 126. Alternatively, slotted openings 112a may either be replaced by or supplemented with rib portions (similar to ribs 212d shown in FIGS. 16–18 and described further herein) formed on the tissue contacting areas of hook portion 112. Cut-out portions 116 are formed at the upper end 118 of frame member 110 to receive a pair of elevation control assemblies 120 therein. Circular cut-out 122 is provided in central portion 124 of frame 110 to attach an adjustable hook member 126 by way of an adjustment knob 128 passing through cut-out 130 formed at the bottom of adjustable hook member 126. Adjustable hook member 126 is further provided with hook portion 132 which curves inwardly through the central opening formed by frame 110. Hook portion 132 is preferably provided with slotted openings 132a to facilitate gripping of bone and/or tissue, thereby preventing lateral movement of hook member 126. Alternatively, slotted openings 132a may either be replaced by or supplemented with rib portions (similar to ribs 212d shown in FIGS. 16–18) formed on the tissue contacting areas of hook portion 132. A rack portion 134 is formed longitudinally along the main surface of adjustable hook member 126.

A large central opening is provided and is defined by inner edge 113. This opening allows the surgeon to insert various surgical instruments through frame member 110 to perform surgical procedures. For example, in the case of a minimally invasive heart bypass procedure, dissectors can be inserted to dissect the IMA for subsequent attachment to another artery.

Figure 5:
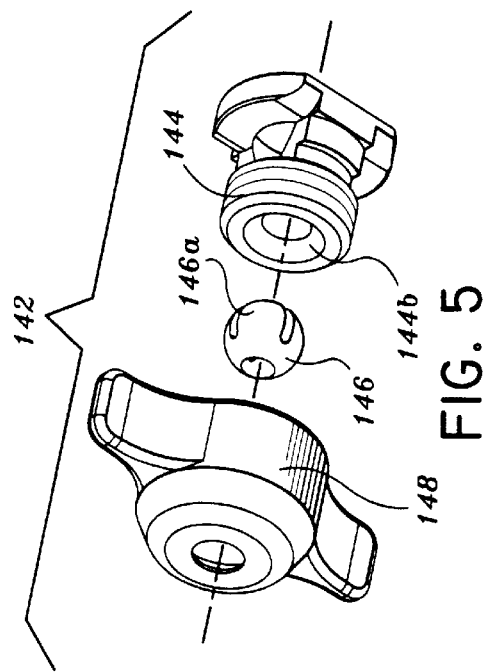
FIG. 5 is a perspective view with parts separated of the locking mechanism of the elevation control assembly of FIG. 4.
Figure 6:
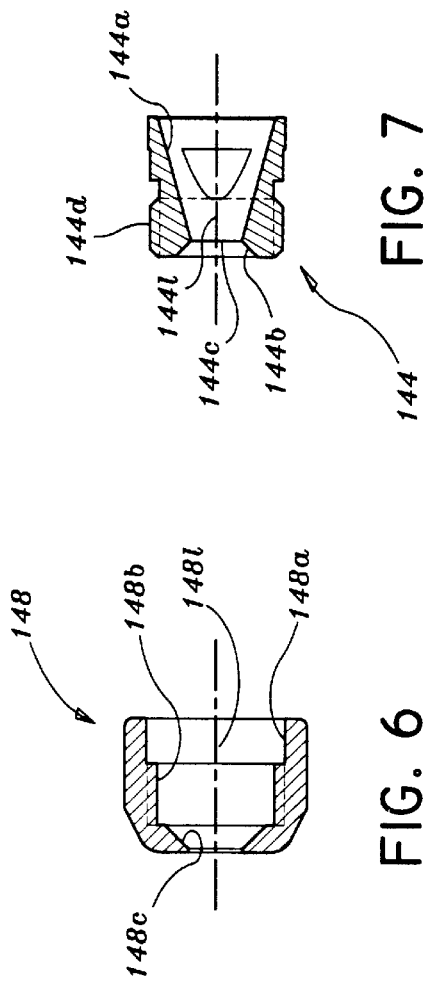
FIG. 6 is a cross-sectional view of a knob-nut of the locking mechanism of FIG. 5.
Figure 4:
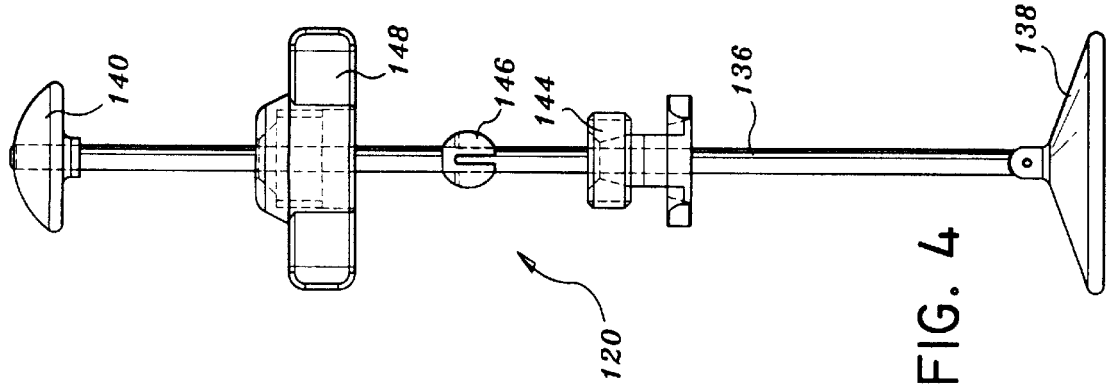
FIG. 4 is a side view of an elevation control assembly of the surgical retractor of FIG. 1.
Figure 9:
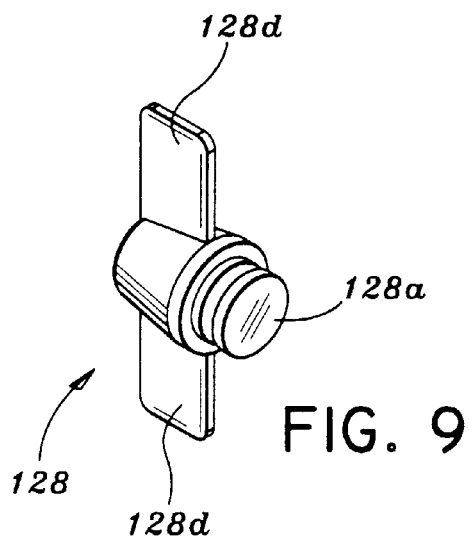
FIG. 9 is a perspective view of the adjustment knob for the adjustable hook of FIG. 8.
Figure 8:
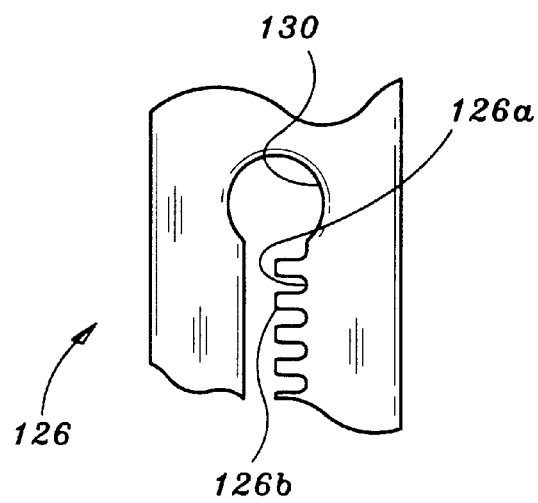
FIG. 8 is a partial view of the adjustable hook member of the surgical retractor apparatus of FIG. 1.
Figure 10:
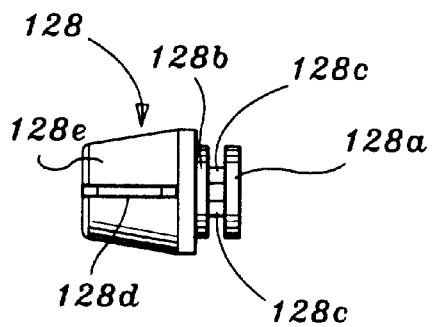
FIG. 10 is a side view of the adjustment knob of FIG. 9.
Figure 11:
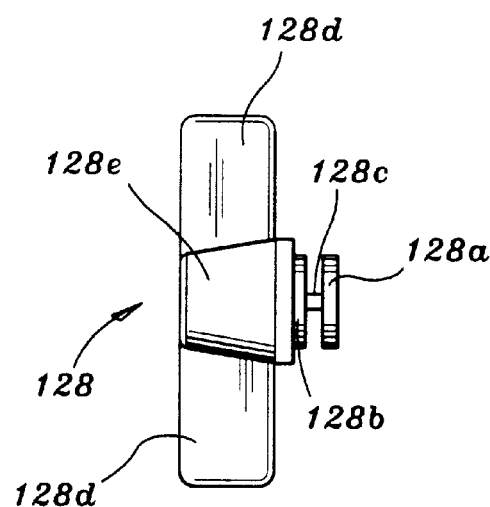
FIG. 11 is a side view of the adjustment knob of FIGS. 9 and 10 taken orthogonally from the view shown in FIG. 10.

Referring now to FIGS. 4–7, the structure and operation of elevation control assemblies 120 will now be discussed in detail. As shown in the assembled view of FIG. 4, elevation control assembly 120 includes an elongated shaft 136 pivotably mounted to a base portion 138 and having a dome-shaped knob 140 to facilitate gripping, attached to the top thereof. A locking mechanism 142, as shown in FIG. 5, is disposed on shaft 136 and includes a collet member 144, a compressible ball-shaped member 146 and a knob-nut 148. Each of these elements includes a central opening of sufficient diameter to permit them to slide along shaft 136 when spaced apart from each other. Knob-nut 148, as shown in FIG. 6, defines a stepped throughbore having adjacent cylindrical step portions 148a and 148b and a frusto-conical portion 148c, each of which are axially aligned along the central longitudinal axis 148L. Portion 148 includes threads formed thereon.

Figure 7:
FIG. 7 is a cross-sectional of the collet of the locking mechanism of FIG. 5.

Referring to FIG. 7, collet member 144 includes a tapered throughbore formed by adjoining frusto-conical sections 144a and 144b which form neck portion 144c at their juncture. Sections 144a and 144b are axially aligned along the central longitudinal axis 144L of collet 144. External threads are formed on the outer surface 144d so as to mesh with the threads formed at step portion 148b of knob-nut 148.

Compressible ball 146 of elevation control assembly 120 includes flexible portions 146a, as shown in FIG. 5, which flex when ball 146 is compressed between frusto-conical surface 144b and frusto-conical surface 148c of the collet 144 and knob-nut 148, respectively. In this manner, when knob-nut 148 is threaded onto collet 144, ball 146 is compressed so that finger portions 146a are biased against shaft 136 so as to lock the locking mechanism 142 and prevent axial movement of the assembly along shaft 136. This locking action prevents axial movement of frame member 110 along shaft 136 as well thereby locking frame member in a fixed position.

Referring to FIGS. 8–11, the adjustment feature of adjustable hook member 126 will now be described in detail. As mentioned above, adjustable hook member 126 includes a cut-out 130 which is configured and dimensioned to receive a circular base 128a of adjustment knob 128. Circular base 128a together with a second circular base 128b form a gap region which is slightly greater than the thickness of the plate material which forms adjustable hook member 126. In this manner, once circular base 128 is passed through cut-out 130, adjustment knob 128 may be slid along adjustable hook member 126 until post members 128c become seated in the first valley 126a which are formed by the gaps between teeth 126b disposed along one side of a longitudinal opening extending along adjustable hook member 126. To facilitate rotation of adjustment knob 128, link portions 128d are formed on opposite sides of hub portion 128e. In this manner, adjustable hook member 126 may be adjusted toward or away from fixed portion 112 by rotating adjustment knob 128 in the desired direction so that post members 128c bias against the sidewalls of teeth 126b and urge adjustable hook member 126 in the desired direction due to the fixed nature of adjustment knob 128 with respect to frame member 110.

In operation of the overall retractor 100, the frame member 110 with the adjustable hook member 126 disposed thereon is inserted between the structures desired to be retracted, for example, in the case of heart surgery the retractor hooks are inserted between the fourth and fifth ribs so that hook portion 132 biases against a first of these ribs and hook portion 112 biases against a second of these ribs in opposite directions. In this position, the retractor frame 112 is substantially parallel to the ribs. Adjustment knob 128 is turned clockwise in the embodiment shown in FIGS. 1–11 to retract hook portion 132 away from hook portion 112 until the desired opening is achieved between the adjacent ribs. The outwardly extending end 118 of frame 110 is then elevated by first loosening locking mechanism 142 on each of the elevation control assemblies 120 and raising end 118 of the frame member so as to elevate one side of the retractor 100.

Once the desired elevation is achieved, locking mechanism 142 is locked as described above to fix the axial location of frame end 118 relative to the shaft 136 of each of elevation control assemblies 120. After the surgical procedure is complete, surgical retractor 100 can be completely disassembled and sterilized for reuse.

Figure 12:
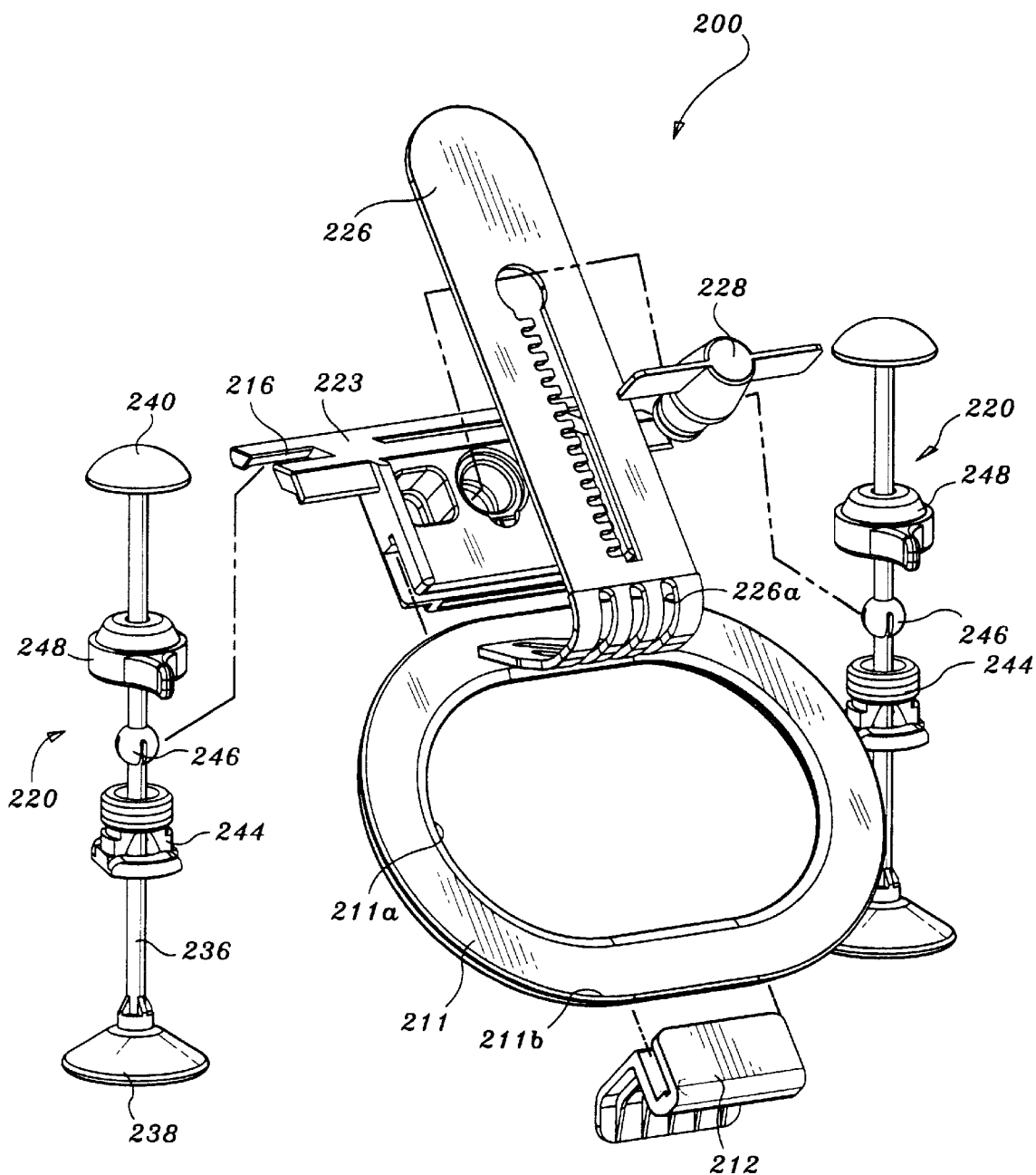
FIG. 12 is a perspective view of a surgical retractor apparatus constructed in accordance with a further embodiment of the present disclosure.

Referring to FIG. 12, a further embodiment of the surgical retractor of the present disclosure is designated generally by reference numeral 200. Preferably, surgical retractor 200 is a disposable assembly which may be discarded after use. Accordingly, the various components of surgical retractor 200 may be made of lightweight polycarbonate materials. However, it is also within the scope of the present disclosure that the various components of surgical retractor 200 may also be made of materials such as stainless steel which may be sterilized and reused if desired.

Surgical retractor 200 includes an oval shaped ring member 211 which defines an inner window area as defined by inner edge 211a. This window area, like the opening in frame member 110 of the previously described embodiment, allows the surgeon to insert various surgical instruments through ring member 211 to perform surgical procedures. Ring 211 further includes a peripheral lip 211b which extends outwardly along the upper outer periphery of ring member 211. Inner edge 211a is preferably beveled inwardly so as to define a smooth surface along the perimeter of the operating window. A removable hook member 212 is snap fitted onto ring member 211 along a first straight portion disposed on one side of ring member 211 and a base portion 223 is similarly snap fitted to a second straight portion disposed on the opposite side of ring member 211. Preferably, removable hook 212 and base 223 are molded parts, each of which will be described in further detail herein. An adjustable hook 226 is attached to base 223 by adjustment knob 228 which snap fits into base 223. Alternatively adjustment knob 228 may be threaded into base 223.

The operation of adjustable hook 226 is similar to that described above in connection with the embodiment of FIG. 1. Accordingly, that operation will not be described in further detail herein. However, it should be noted that adjustable hook 226 which has slotted openings 226a formed thereon to facilitate gripping of tissue and/or bone could be provided with projecting rib portions (similar to rib portions 212d described further herein) either in place of or in conjunction with slotted openings 226a.

A pair of vertical stabilizers 220 are also provided for surgical retractor 200 and are attached to base 223 in openings 216 formed on opposite ends of the base member. Unlike elevation control assemblies 120 of the previously described embodiment, vertical stabilizer members 220 are designed to hold base 223 and therefore, one side of ring member 211 at a fixed elevation relative to bases 238. Otherwise, collet 244, ball 246 and knob-nut 248 work in similar fashion as locking mechanism 142 in order to lock frame member 223 in position relative to the patient's chest wall. It should be noted, that ring member 211 is adapted to have various other instruments connected or attached thereto as desired.

Figure 13:
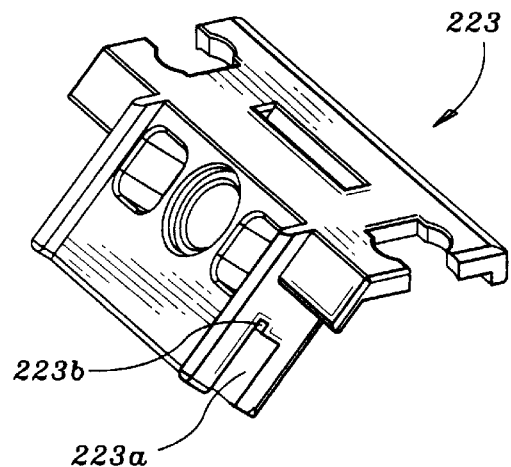
FIG. 13 is a perspective view of a base portion of the surgical retractor apparatus of FIG. 12.
Figure 14:
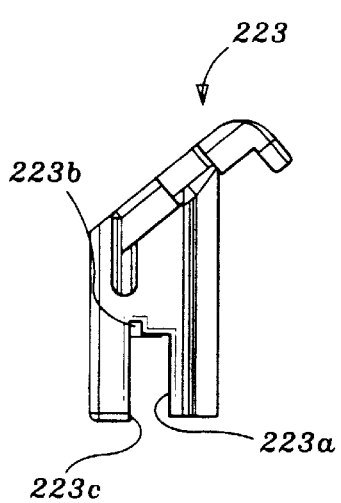
FIG. 14 is a side view of the base portion of FIG. 13.
Figure 15:
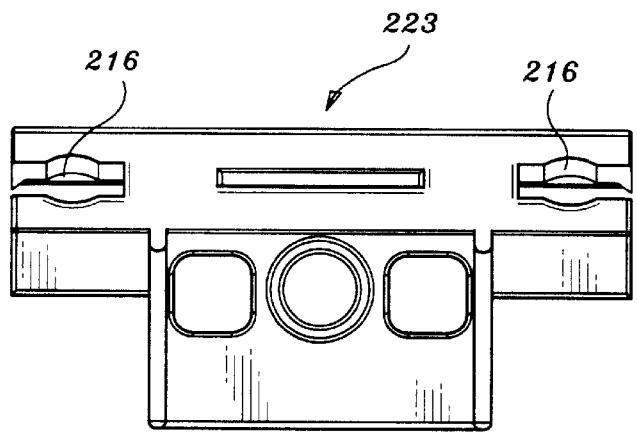
FIG. 15 is a front view of the base portion of FIG. 13.

Referring to FIGS. 13–15, base member 223 is shown having slot 223a formed therein with minor slot 223b formed at the top of slot 223a. Slot 223b facilitates receiving the lip 211b of ring member 211 and lip portion 223c facilitates snap fitting locking type arrangement of base 223 onto ring member 211. Alternatively, ring member 211 could have a peripheral groove formed thereon whereas base 223 and removable hook 212 could each have a projecting lip formed thereon which would facilitate attachment of these elements to ring member 211.

Referring to FIGS. 16–18, removable hook 212 includes an elongated slot 212a formed therein and a minor slot 212b formed therein to facilitate attachment of removable hook member 212 to ring member 211 in a similar manner of attachment of base 223 thereto. Similarly, removable hook member 212 includes a raised surface portion 212c which facilitates the snap fitting of removable hook to the ring 11. Removable hook member 212 is provided with protruding rib portions 212d which extend outwardly from the body contacting surface of removable hook member 212. Rib portions 212d prevent lateral movement of the hook member relative to the contacted body portion, e.g., the rib section. Alternatively, rib portions 212d could be replaced with or supplemented by slotted openings to allow body tissue and/or bone to engage the openings.

It will be understood that various modifications may be made to the embodiment shown herein. Therefore, the above description should not be construed as limiting, but merely as exemplifications of preferred embodiments. Those skilled in the art will envision other modifications within the scope and spirit of the presently disclosed surgical retractor.

What is claimed is:

1. A surgical retractor assembly comprising:
   a frame lying in a first plane and having a first end and a second end, the frame supporting a first hook member on the first end of the frame and a second hook member on the second end of the frame, at least one of the first and second hook members configured to retract tissue in a direction substantially opposed to the other of the first and second hook members; and
   a first elevation control assembly and a second elevation control assembly supporting the frame, each of the first and second elevation control assemblies positioned on either side of the second hook member and configured to be adjusted in a manner to pivot the second end of the frame and the second hook member about the first end of the frame and the first hook member and to selectively retain at least a portion of the frame out of the first plane.

2. The surgical retractor assembly of claim 1, wherein said first hook member is integral with the frame.

3. The surgical retractor assembly of claim 1, wherein said second hook member is removably mounted to the frame.

4. The surgical retractor assembly of claim 1 wherein said second hook member is movable with respect to the frame.

5. The surgical retractor assembly of claim 4, further comprising an adjustment knob for moving said second hook member with respect to the frame.

6. The surgical retractor assembly of claim 1, wherein the frame is substantially rectangular in configuration.

7. The surgical retractor assembly of claim 1, wherein the frame is substantially oval in configuration.

8. The surgical retractor assembly of claim 1, further comprising said second hook member removably mounted to the frame and movable to retract tissue in a direction away from the said first hook member.

9. The surgical retractor assembly of claim 1, wherein the first and second elevation control assemblies each comprise an elongated shaft having a locking mechanism to retain the frame in a selected position.

10. The surgical retractor assembly of claim 1, wherein the first and second elevation control assemblies each include an elongated shaft removably mounted to the frame, each of the elevation control assemblies including a locking mechanism to retain the frame in a selected position.

11. The surgical retractor assembly of claim 10, wherein each locking mechanism includes a collet and a compressible member mounted on the shaft, the collet configured to compress the compressible member onto the shaft.

12. A surgical retractor assembly comprising:

a frame having first and second portions;

a first hook member supported on the frame;

a second hook member supported on the frame and movable with respect to the frame; and a first and a second frame support supporting the frame, the first and second frame supports positioned on either side of the second hook member and adapted to be adjusted in a manner to pivot the frame such that the second hook member pivots about the first hook member and to retain the first portion of the frame in a selected raised position with respect to the second portion of the frame.

13. The surgical retractor assembly of claim 12, wherein the first and second frame supports each comprise an elongated shaft having a locking mechanism for locking the frame in the selected raised position.

14. The surgical retractor assembly of claim 12, wherein the frame includes an opening to provide access to the body tissue.

15. The surgical retractor assembly of claim 12, further comprising a rotatable adjustment knob for moving the second hook member in a direction away from the first hook member.

16. The surgical retractor assembly of claim 13, wherein the locking mechanism includes a compressible member and a collet member, the collet member configured to compress the compressible member against the shaft.

17. The surgical retractor assembly of claim 16, further comprising a rotatable nut threadable onto the collet to compress the compressible member.

18. The surgical retractor assembly of claim 14, wherein the second hook member has a plurality of teeth engagable by the adjustment knob.

19. The surgical retractor assembly of claim 12, wherein the frame includes a base portion removably mounted thereto, and the second hook member is mounted on the base portion.

20. A method for accessing the internal mammary artery in a minimally invasive surgical procedure comprising:

placing a first hook member supported on a frame between ribs of a patient;

placing a second hook member supported on the frame between the ribs;

moving the second hook member in a direction away from the first hook member to retract the ribs;

adjusting two elevation control assemblies connected to the frame on either side of the second hook member to pivot the second hook member about the first hook member and elevate a first portion of the frame away from the patient to a selected raised position; and retaining the first portion of the frame in the selected raised position.

21. The method of claim 20, further comprising the step of inserting a dissector through an opening in the frame to dissect the internal mammary artery.

22. The method of claim 21, wherein the step of moving the second hook member comprises rotating an adjustment knob.

23. The method of claim 22, wherein the step of elevating the first portion of the frame comprises the step of manually sliding the first portion along first and second spaced apart shafts.

24. The method of claim 23, wherein the step of retaining the first portion comprises the step of compressing a compressible member against each of the shafts.

\* \* \* \* \*